[12] United States Patent
Laurenzi

(10) Patent No.: US 9,040,595 B2
(45) Date of Patent: May 26, 2015

(54) PROCESS AND PLANT FOR THE PRODUCTION OF METHANOL WITH ISOTHERMAL CATALYTIC BEDS

(75) Inventor: Fabio Laurenzi, Lugano (CH)

(73) Assignee: Casale SA (CH)

(*) Notice: Subject to any disclaimer, the term of this patent is extended or adjusted under 35 U.S.C. 154(b) by 0 days.

(21) Appl. No.: 13/880,495

(22) PCT Filed: Aug. 4, 2011

(86) PCT No.: PCT/EP2011/063490
§ 371 (c)(1),
(2), (4) Date: Apr. 19, 2013

(87) PCT Pub. No.: WO2012/052204
PCT Pub. Date: Apr. 26, 2012

(65) Prior Publication Data
US 2013/0203872 A1  Aug. 8, 2013

(30) Foreign Application Priority Data
Oct. 22, 2010 (EP) .................... 10188537

(51) Int. Cl.
C07C 29/32 (2006.01)
B01J 8/04 (2006.01)
C07C 29/151 (2006.01)

(52) U.S. Cl.
CPC ............. C07C 29/32 (2013.01); B01J 8/0453 (2013.01); B01J 8/0457 (2013.01); B01J 8/0473 (2013.01); B01J 8/0492 (2013.01); B01J 8/0496 (2013.01); B01J 2208/00274 (2013.01); B01J 2219/00006 (2013.01); B01J 2219/0004 (2013.01); C07C 29/1512 (2013.01)

(58) Field of Classification Search
CPC .... C07C 29/1512; C07C 29/32; C07C 31/04; B01J 2208/00274; B01J 2219/00006; B01J 2219/0004; B01J 8/0453; B01J 8/0457; B01J 8/0473; B01J 8/0492; B01J 8/0496

USPC .................................................. 518/705, 706
See application file for complete search history.

(56) References Cited

U.S. PATENT DOCUMENTS 6,191,175 B1    2/2001  Haugaard et al.
6,214,314 B1 *  4/2001  Abbott ........................ 423/650
2011/0065966 A1 3/2011  Mueller et al.

FOREIGN PATENT DOCUMENTS

EP        1306126 A1    5/2003
WO        01/85331 A1   11/2001
WO        WO2009030353  * 3/2009

OTHER PUBLICATIONS

English translation of wo2009030353, 4 p, 2009.*
International Search Report issued in connection with PCT/EP2011/063490.
International Preliminary Report on Patentability issued in connection with PCT/EP2011/063490.

* cited by examiner

Primary Examiner — Karl J Puttlitz
Assistant Examiner — Amy C Bonaparte
(74) Attorney, Agent, or Firm — Akerman LLP

(57) ABSTRACT

A process for the synthesis of methanol, comprising the steps of reforming a hydrocarbon source obtaining a make-up gas feed (101), feeding said make up gas to a synthesis loop (L), converting said make up gas to methanol (108) in a substantially isothermal catalytic environment, wherein said catalytic environment comprises a plurality of isothermal catalytic beds (11, 12, 21) preferably arranged in series, and at least a portion of make-up gas (101) is mixed with recycle gas (112) from the loop (L), obtaining a gaseous mixture of fresh gas and recycle gas, and at least a portion of said gaseous mixture is directed between two consecutive catalytic beds acting as a quench gas. A related plant is also disclosed.

9 Claims, 1 Drawing Sheet

PROCESS AND PLANT FOR THE PRODUCTION OF METHANOL WITH ISOTHERMAL CATALYTIC BEDS

This application is a national phase of PCT/EP2011/063490, filed Aug. 4, 2011, and claims priority to EP 10188537.4, filed Oct. 22, 2010, the entire contents of both of which are hereby incorporated by reference.

FIELD OF THE INVENTION

The present invention relates to a process and plant for the synthesis of methanol with isothermal reactors.

PRIOR ART

A plant for the synthesis of methanol comprises basically a front end section where a make-up synthesis gas containing carbon monoxide CO and hydrogen $H_2$ is generated by reforming of a hydrocarbon source, and a synthesis loop where said make-up gas is reacted in a catalytic environment at a suitable pressure and temperature, usually 200 to 300° C. and 40 to 150 bar. The loop may comprise one or more reactors, each reactor comprising a catalytic bed contained in a pressure vessel. The synthesis loop delivers a hot gaseous methanol stream which is condensed to obtain liquid crude methanol, which in turn is purified in a distillation section. A gaseous fraction containing hydrogen ($H_2$) is separated from the liquid crude methanol, and at least a part of said gaseous fraction is recycled to the synthesis loop. A part of this gaseous fraction is usually purged from the loop to avoid accumulation of inert gases (inerts) such as argon.

The catalytic synthesis reaction is strongly exothermal and the heat generated by said reaction needs to be removed, in order to avoid overheat and damage of the catalyst.

A known technique is to carry out the reaction in a plurality of adiabatic catalytic beds operating in series, and to remove heat by means of intermediate quenches between said adiabatic beds. A reactor operating comprising several catalytic beds and operating according to this principle is known as quench reactor. A quench reactor typically consists of a number of adiabatic catalyst beds installed in series in one single pressure shell; the reactor feed is split into several fractions and distributed to the synthesis reactor between the individual catalyst beds; the hot effluent of one bed, e.g. the first bed, is quenched by mixing with a respective fraction of the reactor feed, before entering the next (e.g. second) bed. Typically the temperature profile of this reactor is a saw-like curve, the temperature increasing progressively through the catalytic bed and decreasing suddenly where the effluent is mixed with fresh make-up gas.

A drawback of the quench reactor is that a part of the feed bypasses one or more of the catalytic beds, and in that the temperature in the catalytic bed raises with the evolution of the reaction, with a risk of formation of hot spots. This problem is overcome by the isothermal reactors. An isothermal reactor comprises a catalytic bed and a heat exchanger immersed in said catalytic bed, to remove heat directly from the bed and to keep its temperature within an optimal range. An isothermal reactor fitted with a plate heat exchanger is known from EP-A-1284813. A known type of isothermal reactors are axial-radial flow reactors, having a mixed axial and radial flow of reactants through the catalytic bed. An isothermal axial-radial reactor for synthesis of methanol is disclosed for example in EP-A-1306126.

Hence, the prior art provides two alternative techniques to deal with the necessary removal of heat, namely intermediate quench of the gaseous mixture between adiabatic catalytic beds, or direct heat removal by means of heat exchangers immersed in isothermal catalytic beds.

Isothermal reactors are now considered more attractive and, in particular, they are considered more suitable to reach a large capacity (tons of methanol per day). The aforesaid configuration of axial-radial plate reactor, in particular, is advantageous since it reduces the pressure drop of the reactor and allows to increase the capacity of a single reactor/converter, thus reducing the capital cost for a given capacity.

A goal of isothermal reactors is to keep the temperature of the catalytic bed as near as possible to the optimal reaction temperature, avoiding too high peak temperature. The formation of hot spots, i.e. regions where the temperature is higher than nominal may in fact damage the catalyst or at least reduce the efficiency of conversion. This problem is more felt when the make up syngas has a high carbon content, usually in the form of carbon monoxide (CO). A syngas with a high carbon content is found for example in coal-based methanol synthesis, i.e. when the hydrocarbon source of the front-end is coal. Natural gas based reforming produces a synthesis gas with a content of carbon monoxide typically around 5%, while coal based reforming produces a synthesis gas with CO content significantly higher, for example 10% or more.

A gas with a high carbon content is more reactive and then the catalytic bed is, in principle, more exposed to the risk of hot spots and local deviation from the nominal temperature.

This problem is currently faced with measures which, however, introduce some drawbacks. For example, one known measure is to keep a higher concentration of inerts in the synthesis loop, in order to dilute the fresh syngas and make it less reactive. Keeping a higher concentration of inerts affects the efficiency of conversion and increases the flow rate circulating in the loop, which means that, for a given output, larger and more expensive equipments are necessary.

WO 2009/030353 discloses that the synthesis gas is guided through a first, preferably water-cooled reactor, in which part of the carbon oxides is catalytically converted into methanol; the resulting mixture containing synthesis gas and methanol vapor is supplied to a second, preferably gas-cooled reactor, in which a further part of the carbon oxides is converted into methanol; subsequently methanol is separated from the synthesis gas, and the synthesis gas is returned to the first reactor, and a partial flow of the synthesis gas is guided past the first reactor and guided directly into the second reactor. This arrangement however has a drawback in that the stream entering the second reactor has a poor content of fresh gas and hence the reaction remain substantially concentrated in the first reactor.

SUMMARY OF THE INVENTION

The applicant has found that the conversion rate of an isothermal loop is surprisingly improved by introducing intermediate quench of the gaseous flow of reagents and products between isothermal catalytic beds. Said intermediate quench is operated with a gaseous mixture of recycle gas, also called loop gas, and fresh make-up gas. Hence, the fresh make-up gas delivered by the front-end, or at least a portion thereof, is mixed with recycle gas of the loop, and the resulting mixture is merged with the effluent of at least one of the isothermal catalytic beds in the loop.

In a first aspect of the invention, a process for the synthesis of methanol comprises the steps of: obtaining a make-up gas feed from reforming or gasification, feeding said make up gas to a synthesis loop, converting said make up gas to methanol in a catalytic environment while removing heat directly from said catalytic environment, so that said environment is substantially isothermal, condensing said methanol obtaining liquid crude methanol and a recycle gas which is recycled to said synthesis loop, and said process is characterized in that:

said catalytic environment comprises a plurality of isothermal catalytic beds.

at least a portion of said make-up gas feed is mixed with recycle gas, to obtain a gaseous mixture of fresh gas and recycle gas, and at least a portion of said gaseous mixture is directed between a first and a second consecutive catalytic bed of said environment, said gaseous mixture of fresh gas and recycle gas being mixed with the effluent of said first catalytic bed, forming the feed of said second catalytic bed.

In one embodiment, a stream of make-up gas feed is mixed with a stream of recycle gas, to obtain a gaseous mixture of fresh gas and recycle gas; said mixture is split into a plurality of fractions; a first fraction forms the feed of a first catalytic bed, and at least a second stream of said mixture is mixed with the effluent of said first catalytic bed. According to one of possible implementations of this embodiment, the loop comprises three catalytic beds in series, hosted in one or more vessel(s); the make-up gas is mixed with the recycle gas obtained after separation of liquid methanol and purge; the resulting mixture of fresh and recycle gas is split into three portions; one portion is fed to the inlet of the first catalytic bed; a second portion is mixed with the effluent of said first bed, and the third portion is mixed with the effluent of the second bed, forming the feed of the third and last bed.

In another embodiment, make-up gas feed is mixed with recycle gas, to obtain a gaseous mixture of fresh gas and recycle gas, at least a portion is taken from the stream of said mixture, and said portion is mixed with the effluent of a catalytic bed of said catalytic environment.

According to preferred embodiments, the entire flow rate of make-up gas can be mixed with recycle gas.

Said catalytic beds are preferably arranged in series.

The invention is advantageously applied in combination with a front-end delivering a syngas with high carbon (CO) content, for example 10% or higher. A syngas with high carbon content is obtained for example in coal-based production of methanol. Hence, one of the preferred applications of the invention includes that the hydrocarbon source is coal.

A further aspect of the invention is a plant adapted to carry out the above process, where the synthesis loop comprises a plurality of isothermal catalytic beds arranged in series, and a feed line of make-up gas feed joins with a line of recycle gas, to obtain a gaseous mixture of fresh gas and recycle gas, and the plant further comprises a line feeding at least a portion of said gaseous mixture between a first and a second consecutive catalytic bed of the loop, where said gaseous mixture is mixed with the effluent of said first catalytic bed.

In preferred embodiments of the invention, the heat exchangers immersed in the catalytic beds are plate heat exchangers. A preferred application is directed to axial-radial flow catalytic beds, where the flow of reagents is a mixed flow according to both axial and radial direction of the bed. The invention has been found to provide particularly unexpected advantages in combination with axial-radial flow reactors or beds, as will be discussed hereinbelow.

The plurality of isothermal catalytic beds of the synthesis loop can be arranged in one reactor vessel or in a plurality of reactor vessels. Any reactor vessel of the synthesis loop may comprise one catalytic bed or several catalytic beds. For example, in one embodiment of the invention, the loop comprises two reactors in series, namely a first reactor with two separate catalytic beds inside the same pressure vessel, and a second reactor with one catalytic bed.

The invention provides that the catalytic environment of the loop is split into two or more catalytic beds, and further provides intermediate quench of the effluent of one or more catalytic beds of the loop, by means of the mixture of fresh/recycle gas. The invention generally provides the intermediate quench between at least a n-th bed and (n+1)th bed of the loop. In embodiments where the synthesis loop comprises more than two catalytic beds, two or more intermediate quenches are possible. A synthesis loop with n catalytic bed may comprise any number of intermediate quenches from one to (n−1).

The mixing with the quench gas mixture, as defined above, can be effected directly inside a pressure vessel, in embodiments where there is a pressure vessel equipped with two or more catalytic beds.

According to another aspect of the invention, the catalytic beds are of a different volume.

The invention has the following advantages. By combining an intermediate quench with isothermal operation of the catalytic beds, the invention achieves accurate control of temperature and still reduces the risk of hot spots or overheating, without the shortcomings of other measures such as increasing the amounts of inerts in the loop. As a consequence, the catalyst has a longer life and better selectivity, due to optimal temperature of operation. Further to this, the invention has revealed an increase of the overall conversion rate of the loop, contrary to a general belief that intermediate quench, introducing a gas bypass of one or more catalytic beds, would reduce the global efficiency of the synthesis loop and, hence, would not be advisable with isothermal beds.

An aspect of the invention is that fresh make up gas is injected between isothermal catalytic beds, together with recycled loop gas. This feature allows a control of the composition of the gaseous mixture inside the catalytic beds downstream the first bed, i.e. a second and/or a subsequent catalytic bed of the series. In particular, the content of fresh reagents can be regulated for a more efficient exploitation of the available catalytic environment, which means a higher output of methanol.

Further advantages come from the lower flow rate (circulation) in the loop, for a given output of methanol, which is a consequence of the better conversion rate. For a given output, the invention allows to use smaller and less expensive equipments, thus reducing the capital cost. In particular, an advantage of the invention is the use of a smaller gas/gas heat exchanger between effluent and fresh charge. This exchanger is an expensive item, and reducing its size is a considerable advantage.

These and other advantages of the invention will be more evident with the help of the following description of preferred and non-limiting embodiments.

DETAILED DESCRIPTION OF PREFERRED EMBODIMENTS

Figure 1:
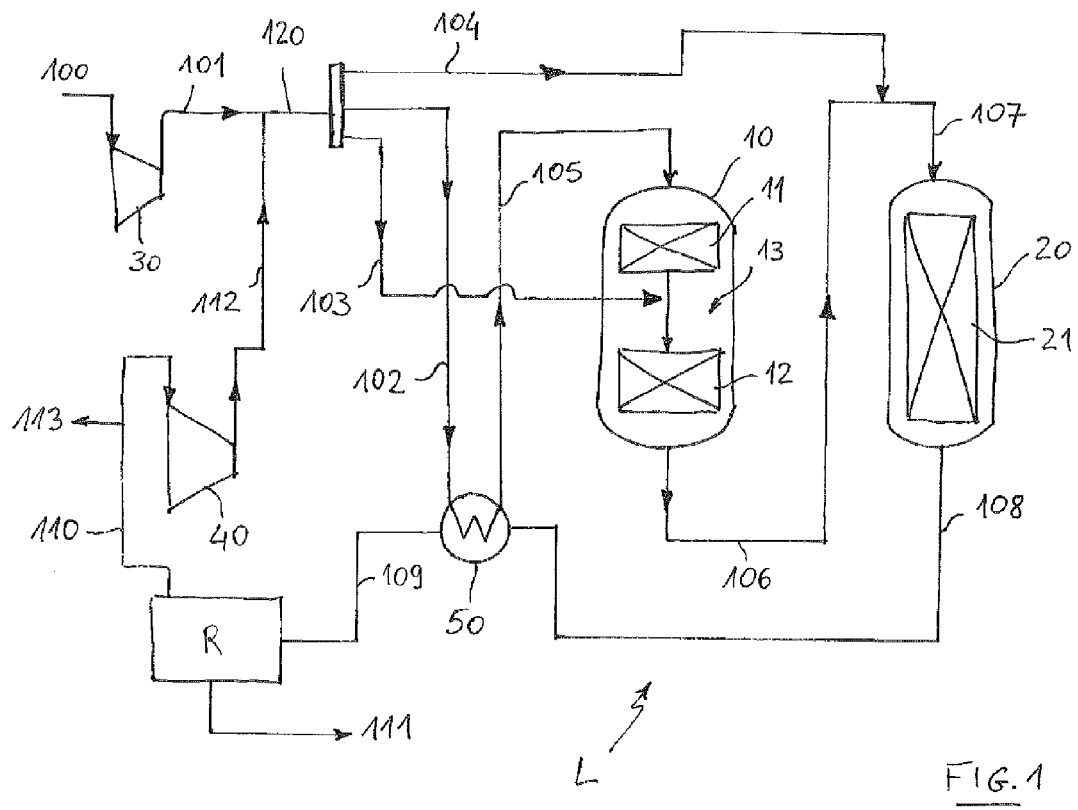
FIG. 1 shows a scheme of a first embodiment of the invention.

With reference to FIG. 1, a methanol synthesis loop L comprises three isothermal catalytic beds arranged in two reactors. A reactor 10 contains two catalytic beds 11 and 12, and a further reactor 20 contains a third catalytic bed 21.

A make-up gas 100 is compressed in a main compression section 30, obtaining a compressed gas feed 101 which, downstream said compression section 30, is mixed with recycle gas 112. The mixture 120 of fresh gas 101 and recycle gas 112 is split into three fractions 102, 103 and 104.

A first fraction 102 forms the gas feed 105 of the first catalytic bed 11, after pre-heating in the gas-effluent heat exchanger 50. The second fraction 103 is mixed with the effluent of said catalytic bed 11, in a space 13 inside the reactor 10 and between the two beds 11 and 12. Hence, said second fraction 103 quenches the effluent of the first bed 11 and helps to control the temperature and the gas composition in the second bed 12. The third fraction 104 is mixed with the effluent 106 of the reactor 10, i.e. effluent of the second bed 12, to form the feed 107 of the second reactor 20 and catalytic bed 21 contained therein. Again, it can be noted that the fraction 104 quenches the hot effluent 106 of the reactor 10 and makes available a certain amount of fresh reagents (mixed with loop gas in the stream 104) in the feed of the second reactor 20 and bed 21.

Hence, the concentration of the reagents in the feed streams of the further catalytic beds 12 and 21 depends not only on the reaction upstream, but is also controlled by the intermediate mixing with streams 103 and 104.

The hot gaseous effluent 108 of the second reactor 20 is raw methanol, which is cooled in the gas/gas heat exchanger 50, while pre-heating the gas fraction 102, obtaining the cooled raw methanol 109. The latter is directed to a section denoted by block R, comprising at least a condenser to obtain liquid crude methanol 111 and to separate a gaseous fraction 110. The liquid methanol 111 is directed to distillation, while the gaseous fraction 110 forms the recycle stream 112, fed to the loop L with the circulator 40. A vent 113 is purged from said gaseous fraction 110, in order to avoid accumulation of inert gases in the loop L.

Figure 2:
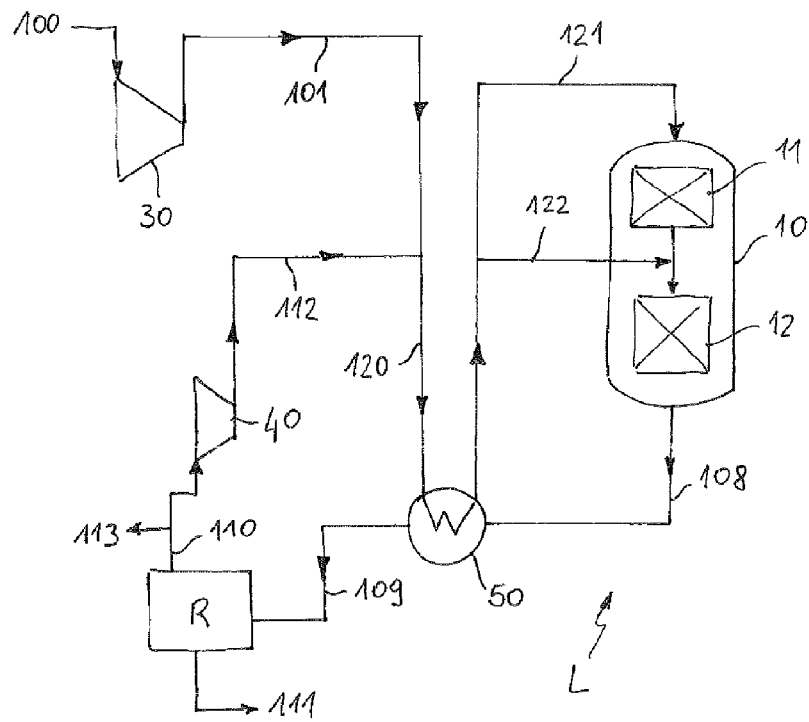
FIG. 2 shows a second embodiment of the invention.

Another embodiment is shown in FIG. 2, referring to an exemplificative layout with two catalytic beds 11 and 12 inside a reactor 10. The feed 101 of make up gas is mixed with recycle gas stream 112, obtaining the mixture 120. In FIG. 2 the full rate of make up gas 101 is mixed with the recycle stream 112, but this is not essential and only a part of said make up gas could be mixed with recycle stream 112, or with a part of said recycle stream. After heating in the exchanger 50, a fraction 121 of the mixture 120 feeds the reactor 10 and then passes through the first catalytic bed 11, and another fraction 122 quenches the effluent of said bed 11. The mixing between effluent of bed 11 and fraction 122 occurs inside the pressure vessel of the reactor 10.

FIG. 2 relates to a preferred embodiment where the quench stream 122 is separated from the gas current 120 after pre-heating in the gas/gas exchanger 50. More generally, a preferred embodiment provides that at least a portion of make-up gas feed is separated after a pre-heating of the make-up gas by heat exchange with the hot effluent of a catalytic bed.

It should be noted that the layouts of both FIGS. 1 and 2 are examples and in particular the number of the catalytic beds, their arrangement in one or more reactors, and the arrangement of the gas quenches, may vary.

EXAMPLE

A conventional loop with two isothermal, axial-radial flow reactors, without quench between reactors, producing 5400 MTD (metric tons per day) of methanol (MeOH), has been compared with a layout similar to FIG. 1, featuring three axial-radial beds arranged in two reactors, all with plate heat exchangers. The invention has shown the ability to increase the conversion rate of methanol, reducing the concentration of inerts in the loop from about 9% to about 7%, and reducing the flow rate in the loop by around 35%.

The following example is a comparison between a known layout, as disclosed e.g. in the aforecited WO 2009/030353, and a layout according to the attached FIG. 1. It can be appreciated that the invention allows an increase in the MeOH outlet, and a significant reduction in the area (UA) of the heat exchanger 50.

|  |  | FIG. 1 | Prior Art |
|---|---|---|---|
| Pure MeOH in the crude | % | 100.0 | 100.0 |
| Catalyst Volume | % | 100.0 | 100.0 |
| Loop Pressure | barg | 83 | 83 |
| MeOH Outlet | % mol | 18.3 | 17.9 |
| Circulation | % | 96.5 | 100.0 |
| Purge Flow | % | 100.0 | 100.0 |
| Gas-Gas UA | % | 75.7 | 100.0 |
| Condensation Duty | % | 100.0 | 98.8 |
| Inerts | % | 108.0 | 100.0 |
| MUG Feed | % | 100.0 | 100.0 |

The invention claimed is:

1. A process for the synthesis of methanol, comprising the steps of obtaining a make-up gas feed from reforming or gasification, feeding said make up gas to a synthesis loop (L), converting said make up gas to methanol in a catalytic environment while removing heat directly from said catalytic environment, so that said environment is isothermal, condensing said methanol obtaining liquid crude methanol and a recycle gas which is recycled to said synthesis loop, wherein:
    said catalytic environment comprises a plurality of isothermal catalytic beds,
    at least a portion of said make-up gas feed is mixed with recycle gas, to obtain a gaseous mixture of fresh gas and recycle gas, and at least a portion of said gaseous mixture is directed between a first and a second catalytic bed of said environment, said gaseous mixture of fresh gas and recycle gas being mixed with the effluent of said first catalytic bed, forming the feed of said second catalytic bed.

2. The process according to claim 1, wherein make-up gas feed is mixed with recycle gas, to obtain a gaseous mixture of fresh gas and recycle gas;
    said mixture is split into a plurality of streams;
    a first of said streams forms the feed of a first catalytic bed, and
    at least a second stream of said mixture is mixed with the effluent of said first catalytic bed.

3. The process according to claim 2, wherein said second stream and any further stream of mixture of fresh gas and recycle gas are mixed with the effluent of a respective catalytic bed of the catalytic environment.

4. The process according to claim 3, the loop comprising three catalytic beds in series, hosted in one or more vessel(s), where make-up gas is mixed with recycle gas and the resulting mixture of fresh and recycle gas is split into three portions;
    one portion is fed to the inlet of the first catalytic bed;
    a second portion is mixed with the effluent of said first bed, and
    the third portion is mixed with the effluent of the second bed, forming the feed of the third bed.

5. The process according to claim 1, wherein the entire make-up gas is mixed with recycle gas.

6. The process according to claim 1, wherein a portion of said gaseous mixture of fresh gas and recycle gas is preheated in a gas/gas heat exchanger and feeds a first catalytic bed of said loop (L).

7. The process according claim 1, said make up gas having a content of carbon monoxide at least 10% in volume, or greater.

8. The process according to claim 7, the make up gas being obtained from reforming of coal.

9. The process according to claim 1, wherein said at least a portion of make-up gas feed is separated after a pre-heating of the make-up gas by heat exchange with the hot effluent of a catalytic bed.

* * * * *